(12) United States Patent
Langer-Anderson et al.

(10) Patent No.: US 11,793,678 B2
(45) Date of Patent: Oct. 24, 2023

(54) BANDAGE COMPOSITION DISPENSER

(71) Applicant: 3M INNOVATIVE PROPERTIES COMPANY, St. Paul, MN (US)

(72) Inventors: Delony L. Langer-Anderson, Hugo, MN (US); Eric M. Chinnock, Chanhassen, MN (US); Junia M. Pereira, Woodbury, MN (US); Jason S. Lind, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 858 days.

(21) Appl. No.: 16/486,059

(22) PCT Filed: Feb. 9, 2018

(86) PCT No.: PCT/IB2018/050815
§ 371 (c)(1),
(2) Date: Aug. 14, 2019

(87) PCT Pub. No.: WO2018/150307
PCT Pub. Date: Aug. 23, 2018

(65) Prior Publication Data
US 2019/0358099 A1    Nov. 28, 2019

Related U.S. Application Data

(60) Provisional application No. 62/458,661, filed on Feb. 14, 2017.

(51) Int. Cl.
*A61F 13/00* (2006.01)
*A61F 15/00* (2006.01)
(Continued)

(52) U.S. Cl.
CPC ...... *A61F 13/00072* (2013.01); *A61F 15/002* (2013.01); *A61J 1/067* (2013.01);
(Continued)

(58) Field of Classification Search
CPC ...... A61M 35/00; A61M 37/00; A61M 31/00; A61M 5/00; A61M 35/003; B05C 17/005;
(Continued)

(56) References Cited

U.S. PATENT DOCUMENTS 1,877,153 A     9/1932  Walter
2,305,899 A *  12/1942  Ritchie ............... B65D 47/44
                                                         401/264
(Continued)

FOREIGN PATENT DOCUMENTS

DE    2948852    11/1981
DE    3531661     5/1987
(Continued)

OTHER PUBLICATIONS

International Search Report for PCT International Application No. PCT/IB2018/050815, dated May 23, 2018, 4 pages.

*Primary Examiner* — Susan S Su
*Assistant Examiner* — Ted Yang

(57) ABSTRACT

Provided is a bandage composition dispenser and/or applicator that includes a nozzle and a cap. In some embodiments, the dispenser and/or applicator is used to dispense a bandage or dressing composition that forms a durable film bandage or skin protectant.

22 Claims, 10 Drawing Sheets

(51) Int. Cl.
*A61M 35/00* (2006.01)
*B05C 17/005* (2006.01)
*B65D 47/12* (2006.01)
*B65D 35/38* (2006.01)
*B65D 35/44* (2006.01)
*B65D 41/02* (2006.01)
*A45D 34/04* (2006.01)
*A61J 1/06* (2006.01)

(52) U.S. Cl.
CPC ..... *A61M 35/003* (2013.01); *B05C 17/00503* (2013.01); *B05C 17/00516* (2013.01); *B65D 35/38* (2013.01); *B65D 35/44* (2013.01); *B65D 41/023* (2013.01); *B65D 47/12* (2013.01); *A45D 34/04* (2013.01)

(58) Field of Classification Search
CPC ........... B05C 5/02; B05C 17/00; B05C 11/00; B05C 17/10; B05C 5/00; B05C 17/00516; B05C 17/00503; B05C 17/00513; B05C 17/00509; B05C 17/00506; B05C 17/002; A61J 1/14; A61J 1/00; A61J 3/00; A61J 1/067; A61F 15/00; A61F 13/00; A61F 13/02; A61F 17/00; A45D 34/04; A45D 40/00; A45D 40/26; B65D 83/00; B65D 35/38; B65D 47/00; B65D 47/20; B65D 35/36

See application file for complete search history.

(56) References Cited

U.S. PATENT DOCUMENTS

| | | | |
|---|---|---|---|
| 2,913,748 A * | 11/1959 | Felter ............... | A47L 23/05 401/264 |
| 3,088,470 A | 5/1963 | Hall | |
| 4,053,243 A * | 10/1977 | Levin ............... | B43M 11/06 401/133 |
| 4,887,924 A * | 12/1989 | Green ............... | B65D 35/36 401/262 |
| 4,957,385 A | 9/1990 | Weinstein | |
| 5,033,647 A | 7/1991 | Smith | |
| 5,073,057 A | 12/1991 | Lathrop | |
| 5,168,935 A | 12/1992 | Thornbury | |
| 5,332,121 A | 7/1994 | Schmidt | |
| 5,577,851 A * | 11/1996 | Koptis ............... | B65D 35/36 401/265 |
| 5,899,893 A | 5/1999 | Dyer | |
| 5,980,495 A * | 11/1999 | Heinz ............... | A61M 5/3202 604/199 |
| 6,090,397 A * | 7/2000 | Lee ............... | A61K 9/7015 424/407 |
| 6,099,807 A * | 8/2000 | Leung ............... | B05D 1/34 422/131 |
| 6,283,933 B1 * | 9/2001 | D'Alessio ............ | A61M 35/003 604/3 |
| 6,340,097 B1 * | 1/2002 | D'Alessio ............ | B05C 17/002 401/196 |
| 6,425,704 B2 * | 7/2002 | Voiers ............... | B65D 83/00 401/196 |
| 6,428,233 B1 * | 8/2002 | Clark ............... | B05C 17/002 401/265 |
| 6,595,940 B1 | 7/2003 | D'Alessio | |
| 7,032,790 B2 | 4/2006 | Williamson, IV | |
| 7,094,250 B2 * | 8/2006 | Stenton ............. | A61M 35/003 222/546 |
| 7,153,053 B1 | 12/2006 | Wiley | |
| 7,449,613 B2 | 11/2008 | Klofta | |
| D646,965 S | 10/2011 | Eason | |
| 8,052,016 B2 * | 11/2011 | Wang ............... | B65D 35/22 222/485 |
| 8,123,423 B2 * | 2/2012 | Houde ............... | A61B 17/00491 401/196 |
| 8,240,482 B2 | 8/2012 | Khan | |
| 8,342,765 B2 * | 1/2013 | Stenton ............. | A61B 17/00491 222/213 |
| 8,516,622 B2 | 8/2013 | Schagen | |
| 8,518,076 B2 * | 8/2013 | Stenton ............. | A61B 17/00491 606/214 |
| 8,550,737 B2 * | 10/2013 | Ruiz, Sr. ........... | A61B 17/00491 401/133 |
| 8,702,751 B2 * | 4/2014 | Stenton ............. | A61B 17/00491 606/214 |
| 8,876,422 B2 | 11/2014 | Lim | |
| 8,979,410 B2 | 3/2015 | Massimi | |
| 9,066,711 B2 * | 6/2015 | Ruiz, Sr. ............ | A61M 35/006 |
| 9,259,757 B1 * | 2/2016 | Santarsiero ......... | B05C 17/0052 |
| D815,944 S * | 4/2018 | Lind ............... | D9/447 |
| 10,478,167 B2 * | 11/2019 | Russo ............... | B05C 17/00583 |
| 10,478,851 B2 * | 11/2019 | Ettlin ............... | B05C 17/002 |
| 2003/0032980 A1 * | 2/2003 | Stenton ............. | A61B 17/00491 606/213 |
| 2005/0025559 A1 * | 2/2005 | Stenton ............. | A61M 35/003 401/266 |
| 2005/0135869 A1 * | 6/2005 | Liberatore ......... | B65D 83/0005 401/266 |
| 2005/0250658 A1 | 11/2005 | Putman | |
| 2006/0065677 A1 * | 3/2006 | Py ................. | B05B 11/1094 222/383.1 |
| 2006/0118005 A1 * | 6/2006 | Hardy ............... | C09J 123/0853 106/600 |
| 2006/0180613 A1 * | 8/2006 | Manesis ............ | B65D 51/1616 222/189.09 |
| 2007/0206988 A1 * | 9/2007 | Washington ......... | A45D 34/042 401/270 |
| 2009/0014481 A1 * | 1/2009 | Benetti ............. | B65D 53/06 222/562 |
| 2009/0045230 A1 * | 2/2009 | Liberatore ......... | B65D 85/72 222/566 |
| 2009/0277912 A1 * | 11/2009 | Wang ............... | B65D 47/2056 220/526 |
| 2009/0324319 A1 * | 12/2009 | Houde ............. | A61B 17/00491 401/138 |
| 2010/0108712 A1 * | 5/2010 | Manesis ............ | B65D 47/2031 222/189.09 |
| 2012/0014909 A1 * | 1/2012 | Chenault .......... | C08G 65/33306 424/78.37 |
| 2014/0086967 A1 * | 3/2014 | Asada ............... | A61L 24/043 525/207 |
| 2014/0234004 A1 * | 8/2014 | Thorpe ............. | A45D 34/041 401/1 |
| 2014/0243727 A1 * | 8/2014 | Gibas ............... | C08K 5/04 602/55 |
| 2016/0015373 A1 * | 1/2016 | Russo ............... | A61B 17/00491 401/268 |
| 2016/0095414 A1 * | 4/2016 | Debnath .......... | B65D 47/243 401/266 |
| 2016/0122088 A1 * | 5/2016 | Jamison ............ | B05C 17/10 401/134 |
| 2016/0175183 A1 * | 6/2016 | Chau ............... | A45D 40/24 601/17 |
| 2016/0200537 A1 * | 7/2016 | Fernandez ......... | B65H 16/005 156/577 |
| 2016/0214121 A1 * | 7/2016 | Ullett ............... | B05C 17/00516 |
| 2016/0296951 A1 * | 10/2016 | Higgins ............ | B05C 17/00516 |
| 2016/0296962 A1 * | 10/2016 | Maxa ............... | A61C 5/62 |
| 2016/0332201 A1 * | 11/2016 | Margoosian ........ | A61M 35/006 |
| 2016/0376069 A1 * | 12/2016 | Jung ............... | B65D 47/06 401/261 |
| 2017/0000823 A1 * | 1/2017 | Abbott ............. | A61K 33/34 |

FOREIGN PATENT DOCUMENTS

| | | | |
|---|---|---|---|
| DE | 10327974 | 1/2005 | |
| KR | 20130101830 | 9/2013 | |
| WO | WO-9923011 A1 * | 5/1999 | ........... A61K 9/7015 |
| WO | WO-0126824 A1 * | 4/2001 | ........... B05C 17/002 |
| WO | WO-02060765 A2 * | 8/2002 | ........ B05C 17/00516 |

(56) References Cited

FOREIGN PATENT DOCUMENTS

| WO | WO 2016-164315 | 10/2016 |
| WO | WO 2016-164316 | 10/2016 |
| WO | WO 2018-071278 | 4/2018 |

\* cited by examiner

BANDAGE COMPOSITION DISPENSER

CROSS REFERENCE TO RELATED APPLICATIONS

This application is a national stage filing under 35 U.S.C. 371 of PCT/IB2018/050815, filed Feb. 9, 2018, which claims the benefit of provisional Application No. 62/458,661, filed Feb. 14, 2017, the disclosure of which is incorporated by reference in its/their entirety herein.

TECHNICAL FIELD

The present disclosure generally relates to a dispenser and/or applicator. In some embodiments, the dispenser and/or applicator includes a nozzle and a cap. In some embodiments, the dispenser and/or applicator is used to dispense a bandage or dressing composition that forms a durable film bandage or skin protectant.

BACKGROUND

3M Company invented easy-to-apply bandage or dressing compositions that dry to form durable film bandages and other tissues protectants such as those described in, for example, PCT Publication Nos. WO 2016/164315 and WO 2016/164316, both of which are incorporated herein in their entirety. These film forming, bandage or dressing compositions can be flexible, breathable, waterproof, non-stinging, gentle to skin, and/or easy to remove by peeling or other wearer generated force. The bandage or dressing compositions, when dried, possess enhanced cohesion and integrity. Accordingly, the film forming compositions are particularly well suited for use as a liquid bandage or skin protectant. The compositions can form a highly conformable bandage. Surprisingly, the bandage or dressing compositions exhibit enhanced water vapor transmission rates (WVTRs) even when applied at a higher coating weight with higher percent solids (and having resultant greater film thickness) than common liquid bandages. Thanks in part to this breathability, the dried films of bandage or dressing composition can enhance skin or wound healing by increasing the rate of wound reepithelization.

In certain advantageous implementations, neither the bandage or dressing composition nor the subsequently-formed films irritate the skin and other tissue during application, drying, or during use after drying. The bandages created are substantially painless while worn and/or can be easily removed by peeling, if desired, substantially without pain or disturbance of the wound or skin site. The bandage or dressing composition, when applied over surfaces moist with blood or body fluids, can form a tough, lightly adherent film that can, in certain circumstances, absorb and retain volumes of exudate. The bandage or dressing composition can also be used with and assist in healing skin conditions such as, for example, eczema, psoriasis, rashes, and burns.

The bandage or dressing compositions can dry to a relatively thick, flexible film with wound healing properties (e.g., breathable, flexible, non-stinging) in a single application. In particular, it is possible that a bandage or dressing composition applied at a 25-120 mil coating thickness to skin at room temperature can form an adherent film having a thickness of at least 2 mils. Once dried on skin, the bandage or dressing compositions can exhibit a 180 degree peel adhesion from human skin of no greater than 900 grams per square inch according to a Skin Adhesion Test and/or a keratin removal level of no greater than 40% according to a Skin Removal Test. Accordingly, the dried films can be removed by application of force without substantial damage to the underlying skin or wound site.

SUMMARY

The viscosity of the bandage or dressing compositions described above depends, in part, on the intended application. For example, where application is to be made to a specific position on the skin (e.g., elbow surfaces, knee surfaces and the like), higher viscosity compositions are preferred to prevent "running" of the compositions to unintended locations. Preferred compositions also possess viscosities that ensure the applied bandage or dressing easily conforms to tissues while drying, does not run, and/or forms a relatively thick film. For some conformable films, the viscosity of the bandage or dressing composition is at least 20,000 Centipoise (cps), at least 50,000 cps, at least 60,000 cps and in yet other embodiments at least 70,000 cps when measured at 23° C. using a Brookfield LVT viscometer and the procedure described in PCT Publication Nos. WO 2016/164315 or WO 2016/164316. In some embodiments, the viscosity is between 100.000 cps and about 800.000 cps when measured at 23° C. using a Brookfield LVT viscometer and the procedure described in PCT Publication Nos. WO 2016/164315 or WO 2016/164316. The inventors of the present disclosure recognized that this is a relatively high viscosity bandage or dressing.

The inventors of the present disclosure also recognized that the bandage or dressing composition is relatively elastomeric and/or sticky. To successfully apply the bandage or dressing composition, the user must "break off" the bandage or dressing from the tip of the dispenser or it will stretch in a long sticky strand or string between the end of the dispenser and the user's skin.

The inventors of the present disclosure also recognized that existing dispensers would not adequately dispense bandage or dressing compositions of a type generally described above. So, the inventors of the present disclosure sought to create a dispenser system and/or applicator that would provide at least some of the following benefits: (1) smooth application of the bandage or dressing composition; (2) consistent application of the bandage or dressing composition; (3) a clean break of the bandage or dressing composition from the dispenser to the user's skin (i.e., no or minimal long sticky strands or strings extending from the dispenser after application); (4) intuitive use by a variety of age and skill level users; (5) cost-effective manufacturing; (6) the required pressure applied to the dispenser to cause it to dispense the bandage or dressing composition is not excessive; (7) the dispenser permits application at a variety of angles; (8) the dispenser can be used in multiple dispenser orientations vis-à-vis the skin to which the bandage or dressing is applied; (9) the dispenser will not harm the area of injury to which it is applying the bandage or dressing composition; (10) the dispenser does not introduce bacteria or germs into the bandage or dressing composition; (11) the dispenser maintains sterility of the bandage or dressing composition; (12) the dispenser can be used well by a left or right handed user. (13) the dispenser can be used well with either a dominant or non-dominant hand of the user, (14) the bandage or dressing will not clog in the dispenser between uses; (15) the dispenser can be used multiple times; (16) the dispenser will seal out air when the dispenser is not in use; (17) the dispenser will keep the bandage or dressing composition in the dispenser when not in use (i.e., there is no or minimal leakage of the bandage or dressing composition from the dispenser when not in use); (18) the dispenser is self-supporting and/or capable of standing on one end, for example, with the tip or dispensing nozzle in a downward position; (19) a user is capable of applying one or more layers that result in a gel bandage that is peelable in its dried state; and/or (20) the dispenser can provide the user with visual and/or tactile feedback as to when the cap is properly positioned on the dispensing nozzle and/or container. The inventors of the present disclosure created novel dispensers that meet at least some of these goals.

Some embodiments of the present disclosure relate to a dispenser according to any of claims 1-22.

The above summary of the present disclosure is not intended to describe each disclosed embodiment or every implementation of the present disclosure. The description that follows more particularly exemplifies illustrative embodiments that can be used in any desired combination whether or not specifically described or shown herein.

BRIEF DESCRIPTION OF DRAWINGS

The disclosure may be more completely understood in consideration of the following detailed description of various embodiments of the disclosure in connection with the accompanying drawings, in which.

In the following detailed description, reference may be made to the accompanying set of drawings that form a part hereof and in which are shown by way of illustration several specific embodiments and/or implementations. It is to be understood that other embodiments or embodiments consisting of combinations of elements described herein are contemplated and may be made without departing from the scope or spirit of the present disclosure. It should be understood that numerous modifications, combinations, and embodiments can be devised by those skilled in the art, which fall within the scope and spirit of the principles of the present disclosure.

DETAILED DESCRIPTION

Various embodiments and implementations will be described in detail. These embodiments should not be construed as limiting the scope of the present application in any manner, and changes and modifications may be made without departing from the spirit and scope of the present disclosure. For example, many of the embodiments, implementations, and examples are discussed with specific reference to bandage or dressing bandage dispensers, but these should not be construed to limit the application scope to this one exemplary implementation. Further, only some end uses have been discussed herein, but end uses not specifically described herein are included within the scope of the present application. As such, the scope of the present application should be determined by the claims.

Dispensers of a type generally described herein include a container that holds the bandage or dressing composition, a nozzle from which the bandage or dressing composition is dispensed, and a cap capable of fitting onto the nozzle when the dispenser is not in use. Various implementations and/or embodiments of such a dispenser is possible within the scope of the present disclosure.

Figure 1A:
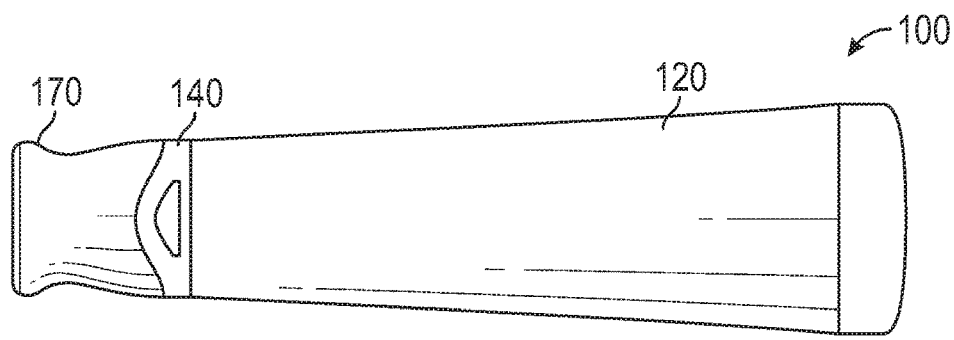
FIGS. 1A and 1B are schematic drawings of an exemplary dispenser of a type generally described in the present disclosure.
Figure 1B:
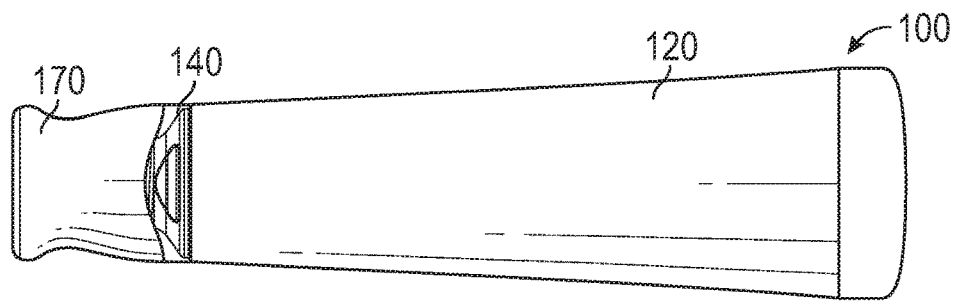
Figure 2A:
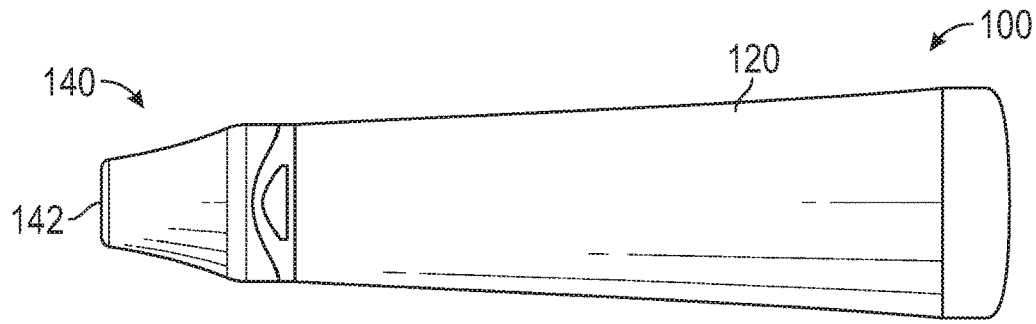
FIGS. 2A and 2B are schematic drawings of the exemplary dispenser of FIG. 1 with the cap removed.
Figure 2B:
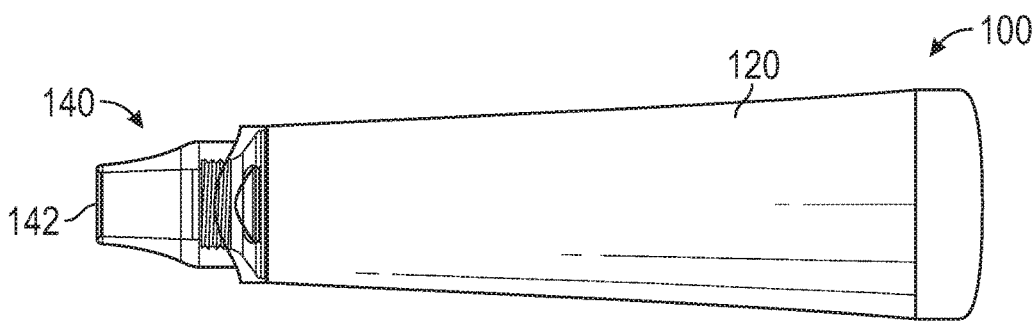

One exemplary dispenser 100 is shown schematically in FIGS. 1A and 1B. Dispenser 100 includes a container 120 that holds the bandage or dressing composition; a dispensing nozzle 140 that is a part of container 120 or connected to container 120 and from which the bandage composition can be dispensed; and a cap 170 that is connected to container 120 or nozzle 140 when the dispenser is not in use. FIGS. 2A and 2B schematically shows dispenser 100 without cap 170 in place. FIGS. 2A and B shows that nozzle 140 includes a slot 142 through which the bandage or dressing composition is dispensed. Detailed information about each of these elements is below. It will be appreciated that the specific implementations of these elements in FIGS. 1A through 2B are merely exemplary and can be modified from what is specifically shown while still falling within the scope of the present disclosure.

Figure 3A:
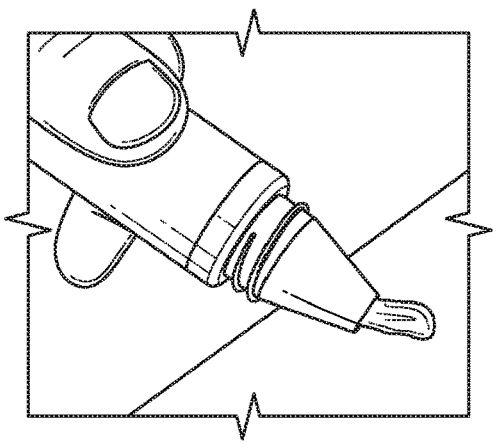
FIGS. 3A and 3B are schematic drawings of a user applying a bandage or dressing composition to his/her skin using the dispenser of FIGS. 1 and 2.
Figure 3B:
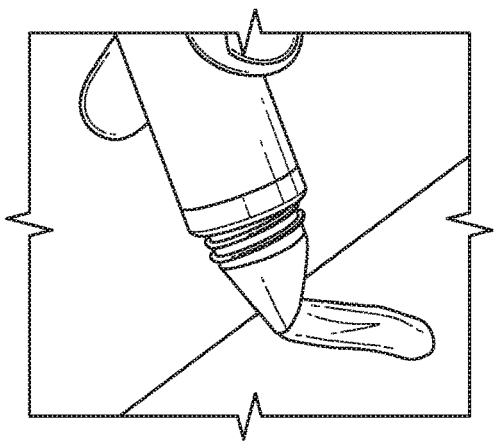
Figure 4:
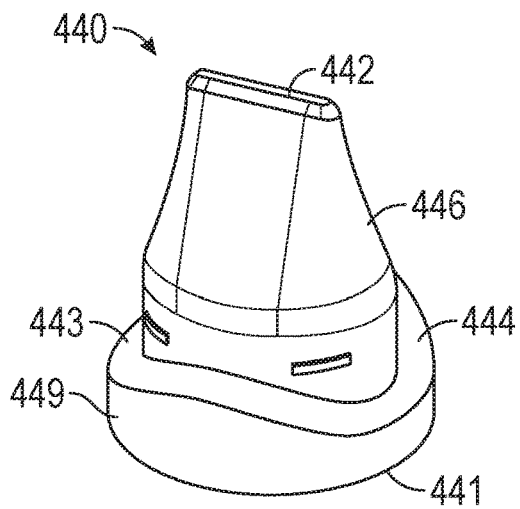
FIG. 4 is a perspective view of an exemplary dispenser nozzle of a type generally described herein.
Figure 5:
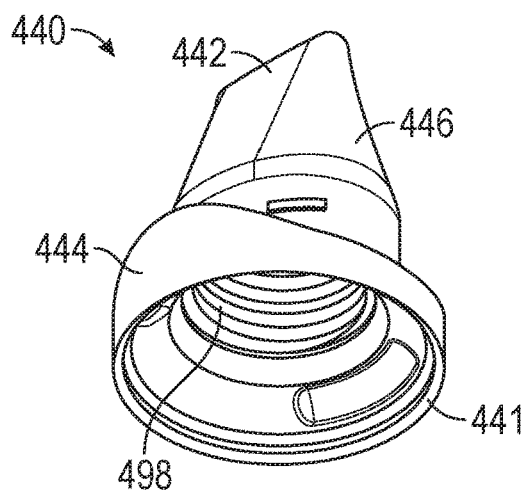
FIG. 5 is a perspective, bottom view of the exemplary dispenser nozzle of FIG. 4.

FIGS. 3A and 3B schematically show two exemplary use procedures for the dispenser 100 of FIGS. 1 and 2. In both FIGS. 3A and 3B, the user is holding container 100 between their thumb and forefinger and squeezing container 100 to cause the bandage composition 398 to be dispensed through slot 142 of nozzle 140 and into the affected area (e.g., wound or skin) 399 of the user. In FIG. 3A, dispenser 100 is held at a roughly 75-90 degree angle relative to the user's affected area. In FIG. 3B, dispenser 100 is held at a roughly 15-40 degree angle relative to the user's affected area. Some embodiments of the present disclosure are capable of being used at all angles between 0 and 180 degrees relative to the user's affected area. Some embodiments are capable of being used at angles between 0 and 90 degrees relative to the user's affected area. Some embodiments are capable of being used at angles between 0 and 40 degrees relative to the user's affected area. Some embodiments are capable of being used at angles between 90 and 180 degrees relative to the user's affected area. Some embodiments are capable of being used at angles between 140 and 180 degrees relative to the user's affected area.

FIGS. 4-9B show various views of an exemplary dispensing nozzle 440 of a type generally described herein. Dispensing nozzle 440 includes, at one terminal end, a slot 442 through which the bandage or dressing composition may be dispensed and, at the opposite terminal end, a nozzle head 444 capable of attachment to a container. Each of an outer nozzle cavity 446 and an inner nozzle cavity 447 extends between slot 442 and nozzle head 444. In alternative embodiments, only a single nozzle cavity is present.

Nozzle head 444 is the portion of dispensing nozzle 440 that connects to or mates with the container. In some embodiments, a lower surface or region 441 of nozzle head 444 may connect or mate with the container. Nozzle head 444 also may also mate or connect with at least a portion of the cap. In some embodiments, an upper surface or region 443 of nozzle head 444 may connect to or mate with a cap.

Upper surface 443 of nozzle head 444 can have any desired aesthetic or decorative shape, dimension, or pattern. For example, the exemplary embodiment show in FIGS. 4-9B has a concave curve 449 on the upper surface 443 of nozzle head 444. In some embodiments, the chosen shape, dimension, or pattern of the upper surface 443 of nozzle head 444 assists in mating dispensing nozzle 440 with a cap. For example, in the exemplary embodiment shown in FIGS. 4-9B, concave curve 449 is capable of mating with the convex curve of cap 1070 of FIGS. 10-15.

Lower surface or region 441 of nozzle head 444 can have any desired shape, size, or dimension and can have any desired aesthetic or decorative shape, dimension, or pattern. For example, the dispensing nozzle can be permanently integrated into the container. This can be accomplished by, for example, ultrasonic welding, gluing or compressing molding. Alternatively, in some embodiments, the nozzle can also be attached to the container through the use of a mechanical or chemical attachment system. One exemplary mechanical attachment system involves a threaded container head that mates with or matches corresponding threads threads on a portion of the dispensing nozzle. These parts can be, for example, molded. Alternatively or additionally, the dispensing nozzle can be snapped into place, in which case the container head would have a permanent snap feature which mates with a portion of the dispensing nozzle for a secure joining.

Dispensing nozzle 444 also includes outer and inner nozzle cavities 446 and 447, each of which can have any desired shape, size, or dimension. Outer nozzle cavity 446 is generally decorative and does not convey, hold, or dispense bandage or dressing composition. Outer nozzle cavity 447 of FIGS. 4-9B has two straight sides 452 and 454 and two curvilinear sides 456 and 458. Curvilinear sides 456 and 458 are slightly concave, but they may be convex in alternative embodiments.

Inner nozzle cavity 447 is capable of being positioned adjacent to the head of the container such that the bandage composition flows from the container directly into inner nozzle cavity 447 and up to slot 442 through which the bandage or dressing composition is dispensed onto a user's wound or skin. The bandage composition entry opening 448 is the aperture or orifice through which bandage or dressing composition from the container enters into inner nozzle cavity 447. Bandage or dressing composition entry opening 448 can be any desired size and shape. In some embodiments, inner nozzle cavity 447 is flush with the head of the container such that little to none of the composition leaks from the intersection of inner nozzle cavity 447 and the container. Inner nozzle cavity 447 of FIGS. 4-9B is cylindrical and has a constant cross-section along its entire length (as shown in, for example, FIG. 6), but any desired shape or cross-section can be used. For example, inner nozzle cavity 447 could have a variable cross-section that more closely follows or mimics the varying cross-section of outer nozzle cavity 446 (see, for example, FIG. 6).

In the specific embodiment of FIGS. 4-9B, the outer surface of inner nozzle cavity 447 includes a screw thread 498 (best shown in FIGS. 5-7) that assists in firmly holding nozzle head 444 onto the container. Other attachment mechanisms can be used, such as, for example, screw-fit together, snapped together, press-fit together, and other similar attachment or connection methods. In some embodiments, the attachment between the nozzle head and the container is air-tight, leakproof, and/or hermetically sealed. In some embodiments, the formation of an air tight seal is quite important because it prevents solvent evaporation from the bandage or dressing composition. If the solvent of the bandage or dressing composition evaporates when the dispenser is not in active use, the number of uses of the container will be limited because the gel composition will no longer have the viscosity needed for application to the user's skin.

Slot 442 can have any desired shape, size, or dimensions, as is described in greater detail below. Slot 442 of FIGS. 4-9B has a length of between about 0.2 inches and about 0.4 inches and a width of between about 0.018 inches and about 0.025 inches. Slot forms the tip of dispensing nozzle 440.

Many changes may be made to specific dispensing nozzle 440 shown in FIGS. 4-9B while still falling within the scope of the present disclosure.

Figure 6:
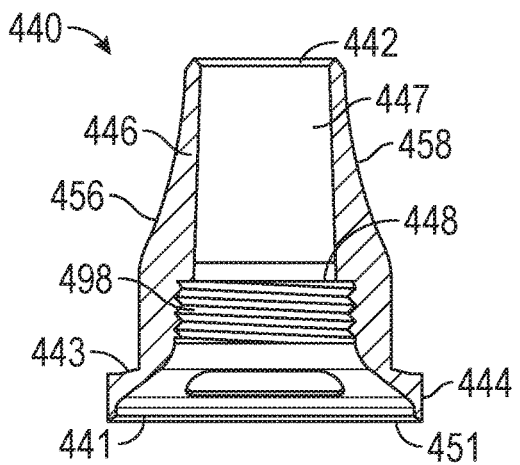
FIG. 6 is a side view of the exemplary dispenser nozzle of FIG. 4.
Figure 7:
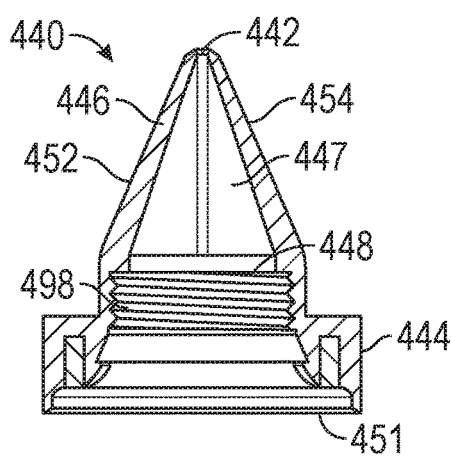
FIG. 7 is another side view of the exemplary dispenser nozzle of FIG. 4.
Figure 8:
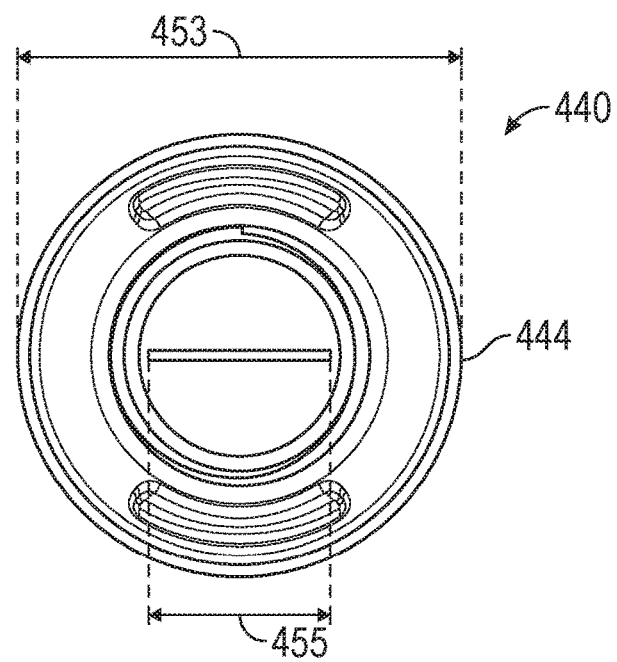
FIG. 8 is bottom view of the exemplary dispenser nozzle of FIG. 4.
Figure 9A:
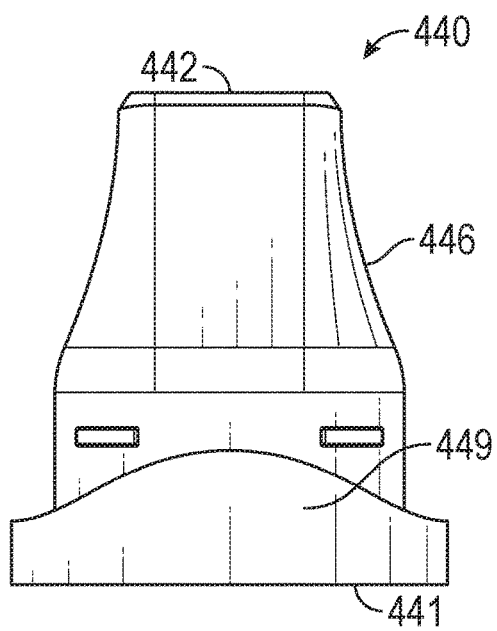
FIGS. 9A and 9B are side views of an alternative exemplary dispenser nozzle.
Figure 9B:
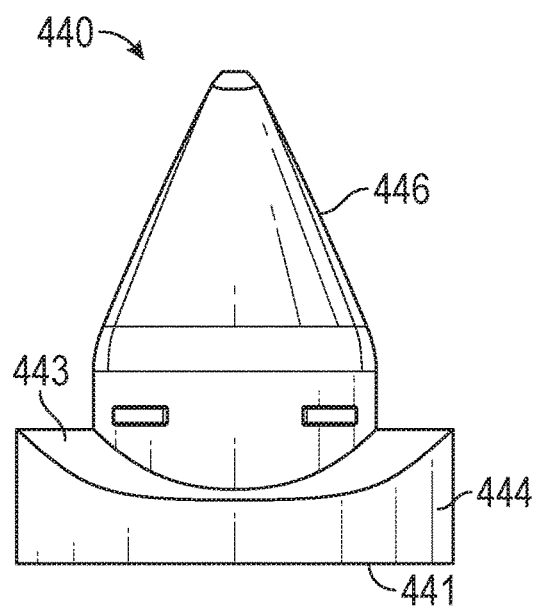
Figure 10:
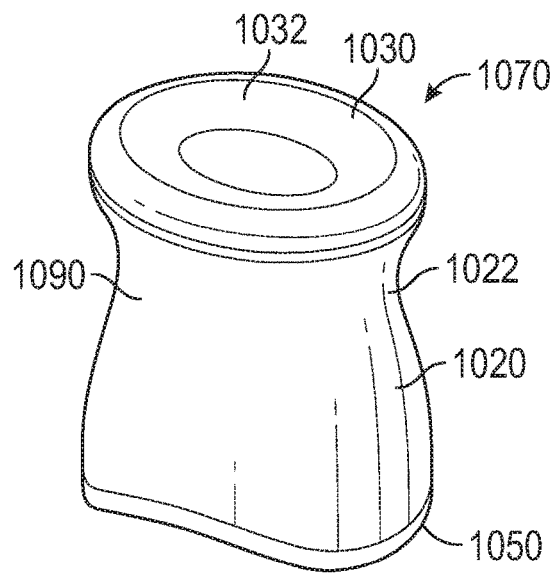
FIG. 10 is a perspective view of an exemplary dispenser cap of a type generally described herein.
Figure 11:
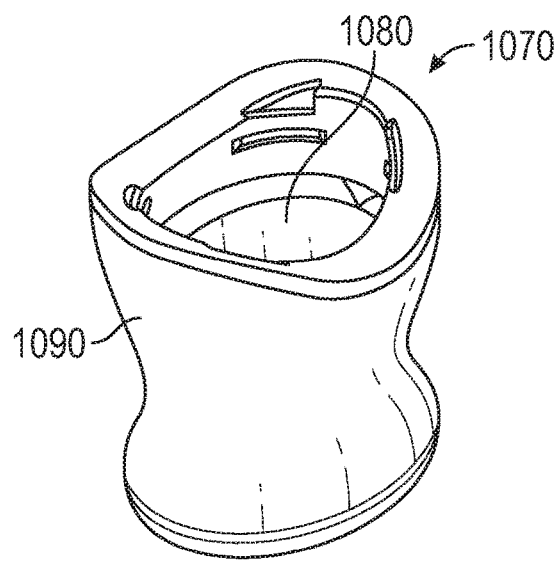
FIG. 11 is a perspective, bottom view of the exemplary dispenser cap of FIG. 10.
Figure 12:
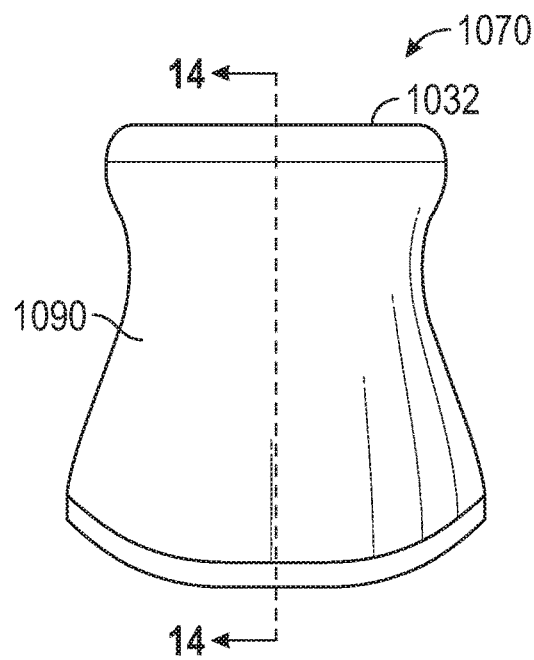
FIG. 12 is a side view of the exemplary dispenser cap of FIG. 10.

FIGS. 9A and 9B are, respectively, schematic side views of dispensing nozzle 440 of FIGS. 6 and 7.

FIGS. 10-16B show various views of an exemplary cap 1070 of a type generally described herein. Cap 1070 is capable of being placed on, attached to, and/or mated with dispensing nozzle 440 of FIGS. 4-9B. Cap 1070 is removable or can be removed from dispensing nozzle 440 of FIGS. 4-9B. Cap 1070 is configured to connect with either or both of the container and/or the dispensing nozzle of the dispenser of which cap 1070 is a part. Cap 1070 includes an interior region 1080 and an outer surface or region 1090.

Figure 13:
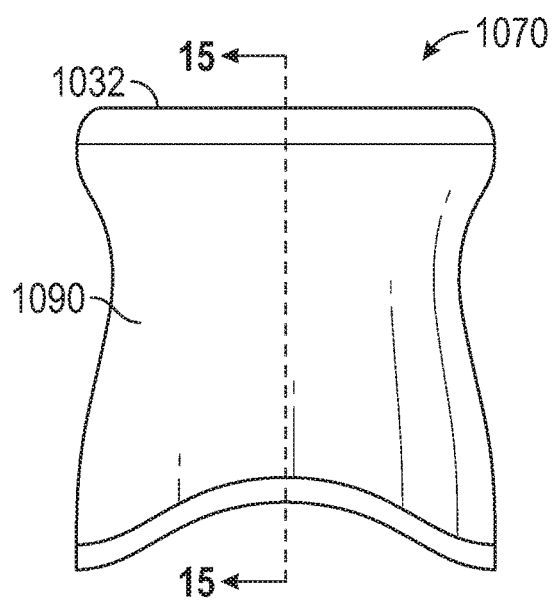
FIG. 13 is another side view of the exemplary dispenser cap of FIG. 10.
Figure 14:
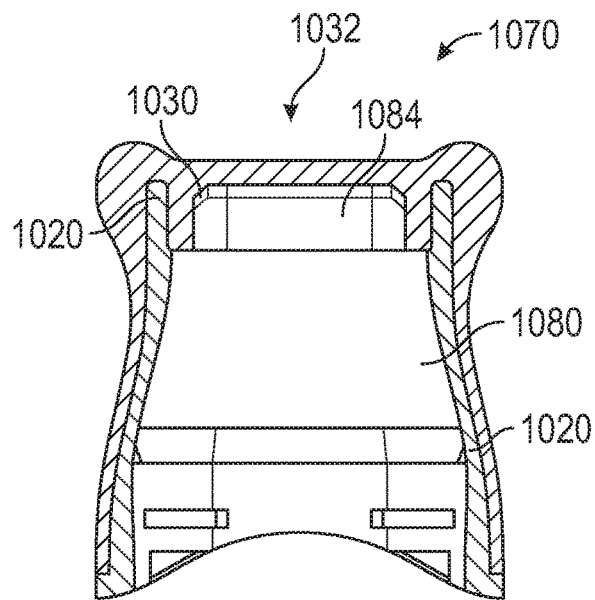
FIG. 14 is side view along section A-A of the exemplary dispenser nozzle of FIG. 10-13.

Outer surface or region 1090 of cap 1070 can match, approximate, and/or mimic the shape of the dispensing nozzle on which the cap is placed or can be different. Cap 1070 of FIGS. 10-16B has curvilinear side walls or surface(s) 1022 that include concave surfaces. Cap 1070 of FIGS. 10-16B includes a curvilinear top or upper surface or region 1032 that includes a concave surface that resembles a divot. Cap 1070 of FIGS. 10-16B includes a curvilinear bottom surface 1050 that includes a concave curve along cross-section B-B as shown in FIG. 13. However, the specific cap design shown in FIGS. 10-16B is merely exemplary and many changes may be made to it while still falling with the scope of the present disclosure.

Cap 1070 includes a less or nonconformable portion or region 1020 including or made of a less or nonconformable material and a conformable portion or region 1030 made of a more or conformable material. In some embodiments, nonconformable portion or region 1020 includes the side walls or surface(s) 1022 of cap 1070. In some embodiments, conformable portion 1030 includes the top surface or region 1032 of cap 1070. Unlike existing caps, the top surface or region 1032 includes only or solely the conformable material. To be clear, cap 1070 of FIGS. 10-16B is not made of a less or nonconformable material that is subsequently at least partially filled with a softer material. Instead, a portion (e.g., the top surface or region 1032) of cap 1070 is made solely of the conformable material.

In some embodiments, the side walls or surface(s) 1022 of cap 1070 include a nonconformable material (e.g., a harder, less resilient material) while the top or upper surface or region 1032 of cap 1070 does not include the nonconformable material. In some embodiments, including the embodiment shown in FIGS. 10-16B, the side walls include both the conformable material and the less or nonconformable material. Specifically, in the cap of FIGS. 10-16B, the side walls or surface 1022 include a region of nonconformable material 1020 directly adjacent to interior region 1080 of cap 1070 and a region of conformable material 1030 directly adjacent or on top of nonconformable material 1020.

In some embodiments, the conformable portion or region 1030 has a Shore A hardness of between about 20 and about 70 as measured by ASTM D2240-15 Standard Test Method for Rubber Property—Durometer Hardness. In some embodiments, the conformable portion or region 1030 has a hardness of between about 25 and about 35 A as measured by ASTM D2240-15 Standard Test Method for Rubber Property-Durometer Hardness. In some embodiments, conformable portion or region 1030 includes at least one of thermoplastic polymer, a silicone, a thermoset elastomer, rubber, thermoplastic urethane, and similar materials. In some embodiments, the less or nonconformable portion or region 1020 has a shore A hardness of at least 1.2 times or 1.5 times or 1.7 times or 2.0 times, or 2.3 times, or 2.5 times, or 3 times the shore A hardness of the conformable portion as measured by ASTM D2240-15 Standard Test Method for Rubber Property—Durometer Hardness. In some embodiments, the less or nonconformable portion or region 1020 has a hardness of at least about 24, or at least 28, or at least 30, or at least 35, or at least 40, or at least 45, or at least 50 shore A as measured by ASTM D2240-15 Standard Test Method for Rubber Property—Durometer Hardness. In some embodiments, less or nonconformable portion of region 1020 includes at least one of thermoplastic (e.g., polypropylene), a resin, a thermoset plastic, urethane, acrylonitrile butadiene styrene, polytetrafluorethylene, and/or a metal.

Figure 15:
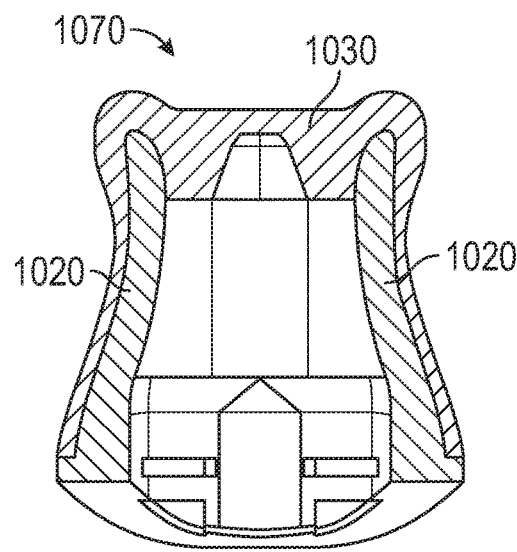
FIG. 15 is side view along section B-B of the exemplary dispenser nozzle of FIGS. 10-14 on the exemplary dispenser cap of FIG. 4.
Figure 16A:
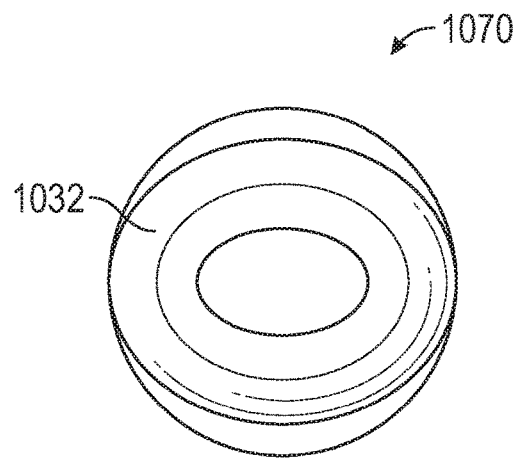
FIGS. 16A and 16B are respective top and bottom views of the exemplary dispenser cap of FIGS. 10-13.
Figure 16B:
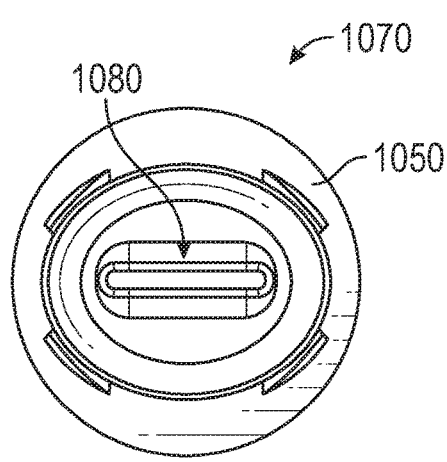

Cap 1070 also includes an inner or interior region 1080 having a size and shape that makes it amenable to being placed over a corresponding dispensing nozzle. More specifically, cap 1070 is shaped and sized to fit over dispensing nozzle 440, so interior region 1080 of cap 1070 is sized slightly larger than the outer dimensions of dispensing nozzle 440. Inner region 1080 includes a preformed recess 1084. The preformed recess is made of a conformable material that forms an abutment surface 1086 that sealingly engages the preformed slot when the cap is attached to, mated with, or placed adjacent to the dispensing nozzle. The conformability of the conformable material assists in creating a seal between abutment surface 1086 and the slot of the dispensing nozzle. FIG. 15 shows a cross-sectional view of dispensing nozzle 440 mated with cap 1070 such that slot 442 sealingly engages with abutment surface 1086 of recess 1084 of interior region 1080 of cap 1070. This sealed engagement forms a tight seal.

In some embodiments, inner region 1080 is configured to generally match, approximate, mate with, engage with, correspond with, and/or mimic, the corresponding size and shape of dispensing nozzle 440. In some embodiments, the nozzle and the recess have matching, mating, engaging, complementary, and/or corresponding abutment surfaces. In some embodiments, the abutment surfaces of the recess and the nozzle sealingly engage. In some embodiments, the cap has a closure surface region adjacent to the slot portion of the dispenser, thereby preventing flow of bandage material from the slot. In some embodiments, the recess is a negative imprint or impression of the nozzle. In some embodiments, the dispensing nozzle include a pair of opposed angled surfaces and the recess includes a complementary opposed angled surfaces. In some embodiments, the cap is so dimensioned to fit over the dispensing nozzle. In some embodiments, the dispensing nozzle is so dimensioned to fit within the cap. In some embodiments, the slot and recess are so dimensioned to provide a seal that prevents or minimizes the material in the container from leaking from the slot when the cap and dispensing nozzle are paired or mated.

Figure 17:
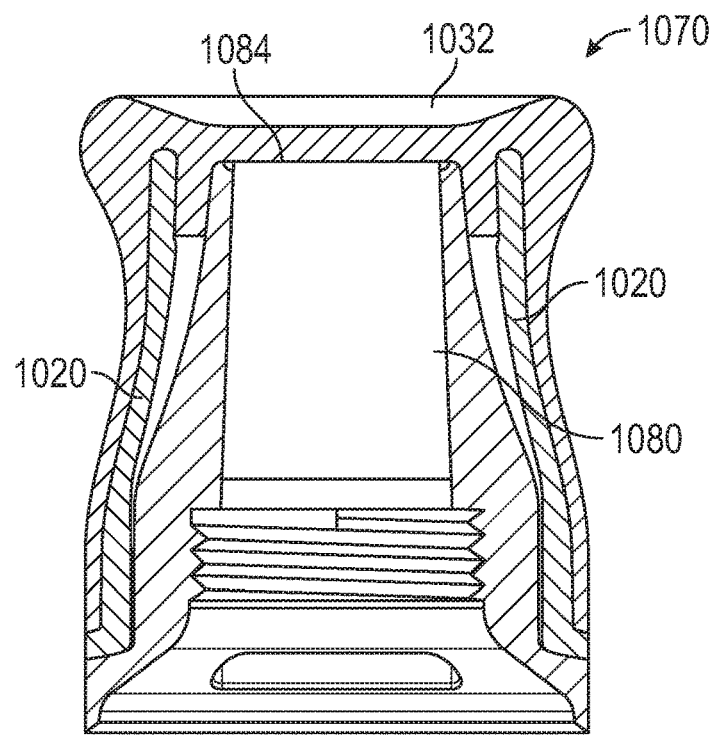
FIGS. 17 and 18 are cross-sectional side views of the dispenser nozzle and cap combination of FIGS. 4-16B mated, attached, or adjacent to one another.
Figure 18:
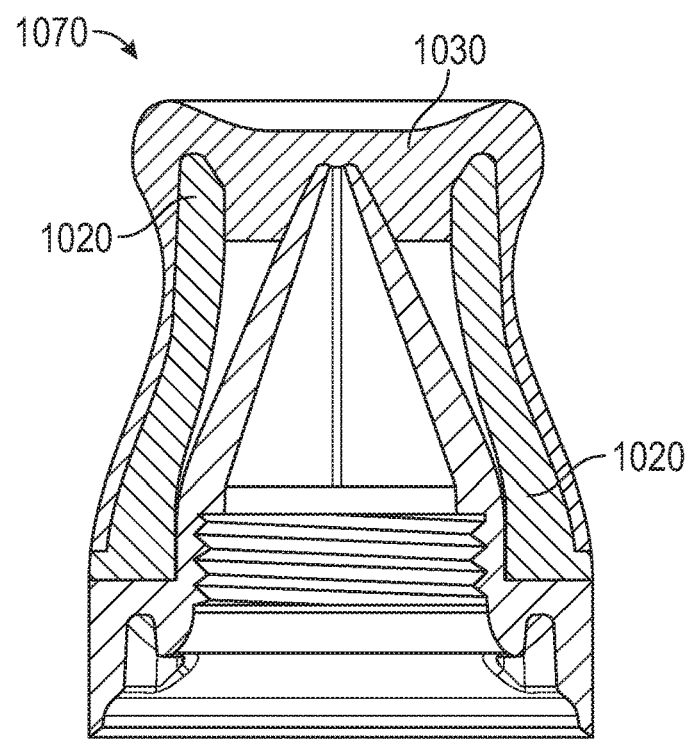

FIGS. 17 and 18 are cross-sectional side views of dispensing nozzle 440 and cap 1070 of FIGS. 4-16B mated, attached, or adjacent to one another.

Figure 19:
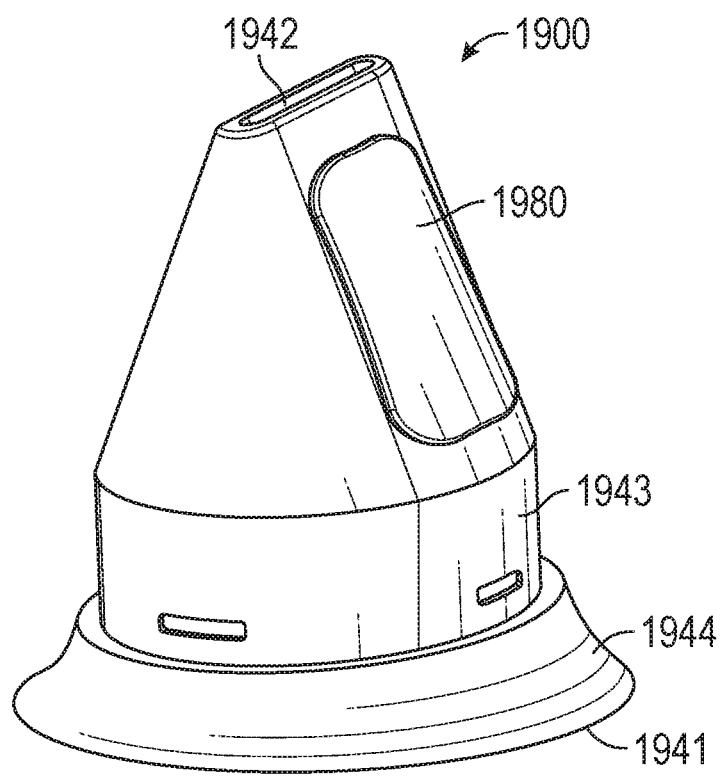
FIGS. 19-21 are respective perspective and side views of an alternative exemplary dispenser nozzle of a type generally described herein.
Figure 20:
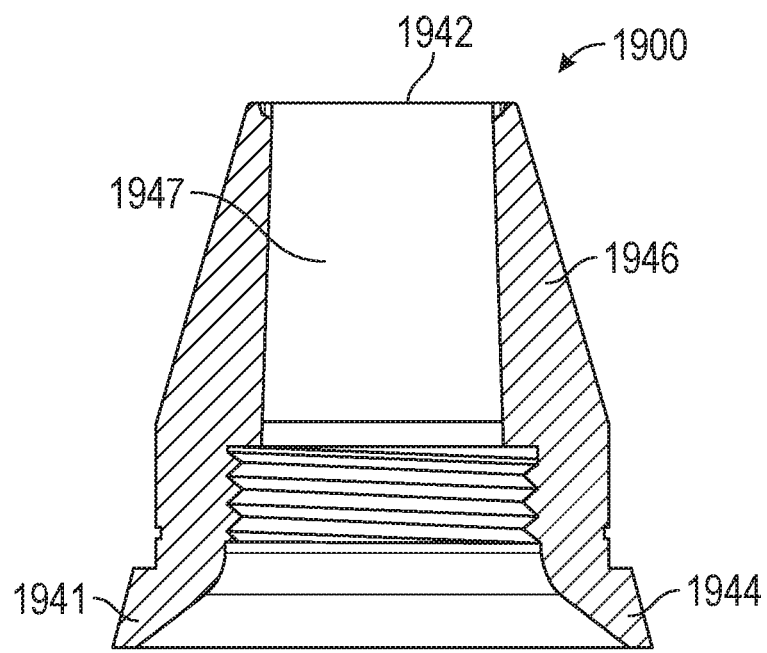
Figure 21:
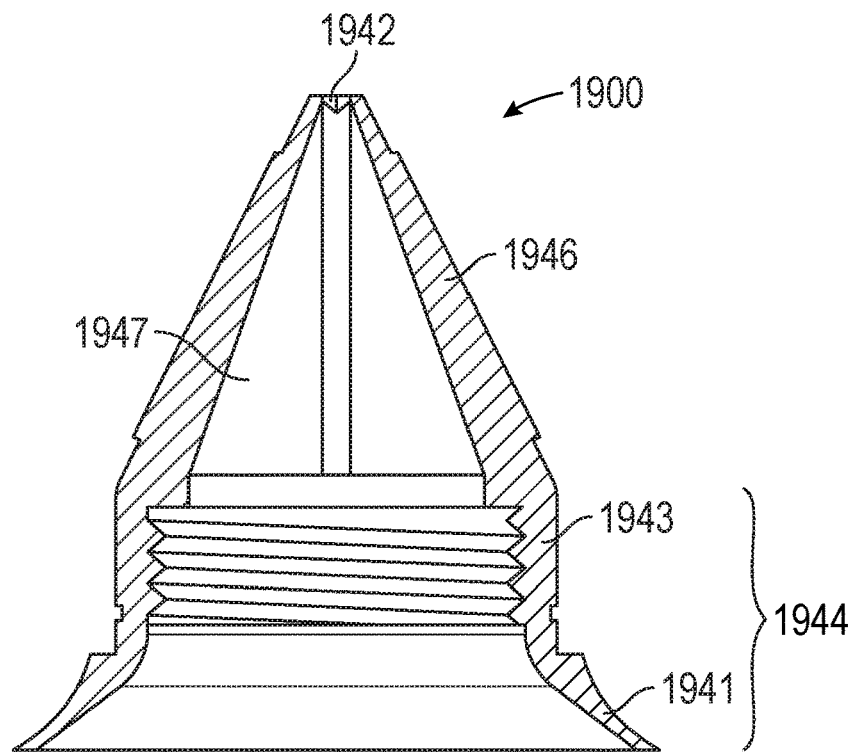

FIGS. 19-21 show an alternative embodiment of an exemplary dispensing nozzle of a type generally described herein. Dispensing nozzle 1900 includes, at one terminal end, a slot 1942 through which the bandage or dressing composition may be dispensed and, at the opposite terminal end, a nozzle head 1944 capable of attachment to a container. Each of an outer nozzle cavity 1946 and an inner nozzle cavity 1947 extends between slot 1942 and nozzle head 1944.

Nozzle head 1944 is the portion of dispensing nozzle 1940 that connects to or mates with the container. Nozzle head 1944 also may also mate or connect with at least a portion of the cap. In some embodiments, a lower surface or region 1941 of nozzle head 1944 may connect or mate with the container. Lower surface or region 1941 of nozzle head 1944 can have any desired shape, size, or dimension and can have any desired aesthetic or decorative shape, dimension, or pattern. For example, the exemplary embodiment show in FIGS. 19-21 has a threaded tube head on the container that mates with threads on the dispensing nozzle. However, other attachment mechanisms can be used to connect the container and dispensing nozzle.

Inner nozzle cavity 1947 is capable of being positioned adjacent to the head of the container such that the bandage composition flows from the container directly into inner nozzle cavity 1947 and up to slot 1942 through which the bandage or dressing composition is dispensed onto a user's wound or skin. In some embodiments, inner nozzle cavity 1947 is flush with the head of the container such that little to none of the bandage or dressing composition leaks from the intersection of inner nozzle cavity 1947 and the container. Inner nozzle cavity 1947 of FIGS. 19-21 is cylindrical and has a constant cross-section along its entire length (as shown in, for example, FIG. 20), but any desired shape or cross-section can be used. For example, inner nozzle cavity 1947 could have a variable cross-section that more closely follows or mimics the varying cross-section of outer nozzle cavity 1946 (see, for example, FIG. 20).

In the specific embodiment of FIGS. 19-21, the outer surface of inner nozzle cavity 1947 includes a screw thread 1949 (best shown in FIGS. 20 and 21) that assists in firmly holding dispensing nozzle 1900 onto the container. Other attachment mechanisms can be used, such as, for example, screw-fit together, snapped together, press-fit together, and other similar attachment or connection methods. The various embodiments of attachment of the dispensing nozzle to the container described above and herein can also be used with this embodiment or implementation. In some embodiments, the seal or attachment between the dispensing nozzle 1900 and the container is air-tight, leakproof, and/or hermetically sealed.

Slot 1942 can have any desired shape, size, or dimensions, as is described in greater detail herein. Slot 1942 forms the tip of dispensing nozzle 1900.

Dispensing nozzle 1900 of FIGS. 19-21 also includes a tapping surface 1980 (shown in FIG. 19). Tapping surface 1980 is an area or region of dispensing nozzle 1900 that can be used by the user to tap down or smooth the bandage or dressing composition after application on the user's skin or wound. The specific tapping surface implementation shown in FIG. 19 is on the outer surface of outer nozzle cavity 1946. It can be on one or more sides or surfaces of the outer surface of outer nozzle cavity 1946. It can occupy any desired amount of surface area of the outer surface of outer nozzle cavity 1946. It can be made of the same material as the outer surface nozzle cavity (e.g., a conformable material) or can be made of a different material. Some exemplary different materials include materials with a surface energy lower than 35 dynes/cm$^2$. Some exemplary materials include, for example, polypropylene, acrylonitrile butadiene styrene, polytetrafluorethylene, and other similar materials.

Many changes may be made to specific dispensing nozzle 1900 shown in FIGS. 19-21 while still falling within the scope of the present disclosure.

Figure 22:
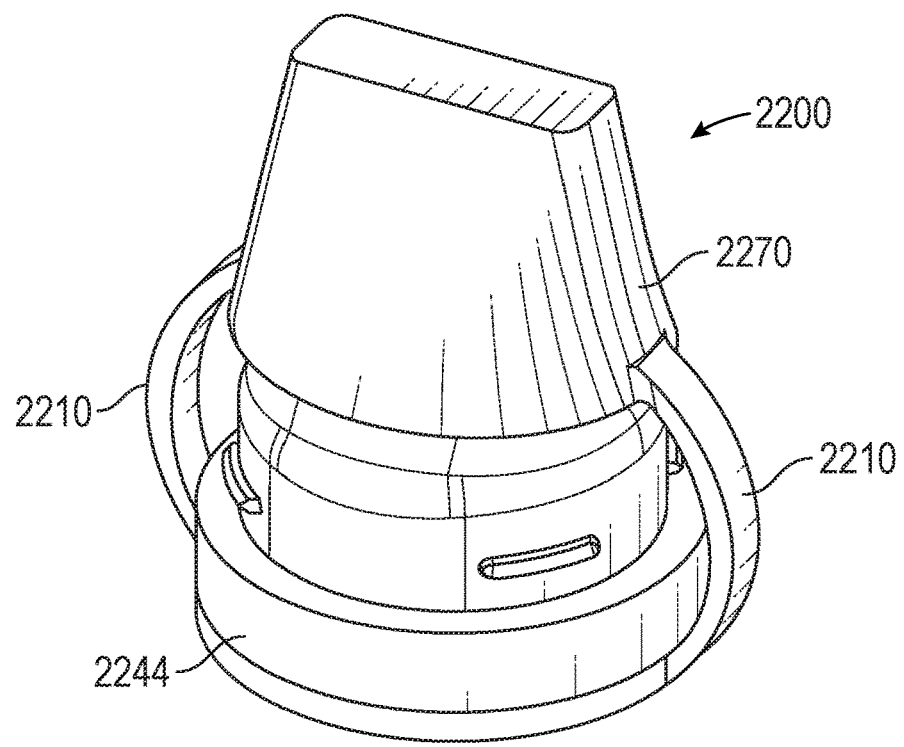
FIGS. 22 and 23 are respective perspective and side views of an alternative exemplary dispenser nozzle of a type generally described herein.
Figure 23:
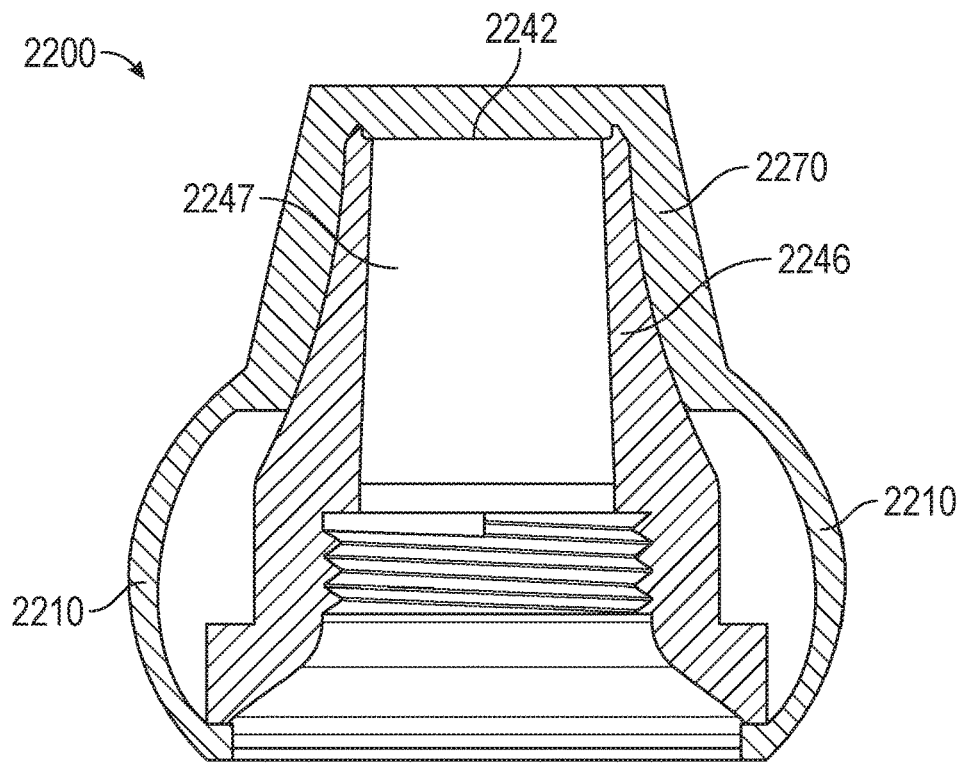

FIGS. 22 and 23 show various views of an alternative embodiment of an exemplary dispensing nozzle 2200 and cap 2270 combination. Dispensing nozzle 2200 includes, at one terminal end, a slot 2242 through which the bandage or dressing composition may be dispensed and, at the opposite terminal end, a nozzle head 2244 capable of attachment to a container. Each of an outer nozzle cavity 2246 and an inner nozzle cavity 2247 extends between slot 2242 and nozzle head 2244. Nozzle head 2244 is the portion of dispensing nozzle 2200 that connects to or mates with the container.

The dispensing nozzle 2200 and cap 2270 combination of FIGS. 22 and 23 is, in many ways, similar to other dispensing nozzle/cap combinations shown and/or described herein. Some differences of are as follows. Cap 2270 covers a smaller or lower total surface area of dispensing nozzle 2200 than other caps shown or described herein. Cap 2270 rests on or is adjacent to sides 2256, 2258 of outer nozzle cavity 2246 instead on nozzle head 2244. The shape of cap 2270 differs from those shown in other figures herein. Cap 2270 includes one or more tethers 2210 extending from the lower portion of cap 2270 to a portion of nozzle head 2244.

Tethers 2210 and cap 2270 can be made in a single operation or in multiple operations. In some embodiments, the tethers are made of or include a stretchy, conformable material such as those listed above. Exemplary manufacturing processes include injection molding, compression molding, and/or casting. In some embodiments, the recess is preformed. In some embodiments, the cap is or can be removed by stretching the tethers until the cap is clear of the nozzle and can be slid off to the side of the nozzle. To reapply the cap, one would stretch the tether until the cap was over the nozzle, and then the slot of the dispensing nozzle was able to slide into the recess.

Many changes may be made to specific dispensing nozzle 2200 and cap 2270 combination shown in FIGS. 22 and 23 while still falling within the scope of the present disclosure.

Figure 24:
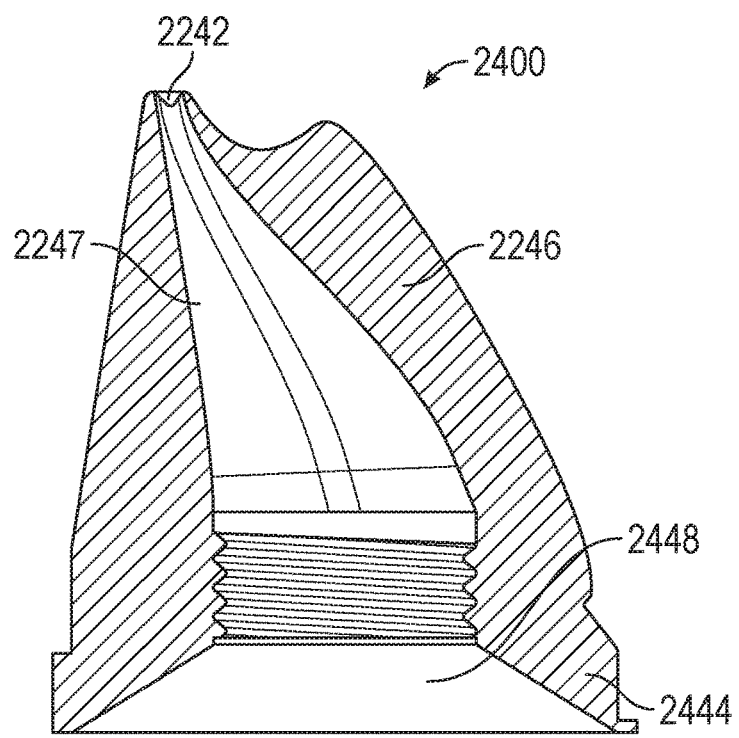
FIG. 24 is a side view of an alternative exemplary dispenser nozzle of a type generally described herein.

FIG. 24 show a cross-sectional schematic view of an alternative embodiment of an exemplary dispensing nozzle of a type generally described herein. Dispensing nozzle 2400 includes, at one terminal end, a slot 2442 through which the bandage or dressing composition may be dispensed and, at the opposite terminal end, a nozzle head 2444 capable of attachment to a container. Each of an outer nozzle cavity 2446 and an inner nozzle cavity 2447 extends between slot 2442 and nozzle head 2444. Nozzle head 2444 is the portion of dispensing nozzle 2440 that connects to or mates with the container. Bandage composition entry opening 2448 is the aperture or orifice through which bandage or dressing composition from the container enters into inner nozzle cavity 2447.

The dispensing nozzle 2400 of FIG. 24 is, in many ways, similar to other dispensing nozzles shown and/or described herein. Some differences of are as follows. Inner nozzle cavity 2447 decreases in diameter or width along its length with its smallest diameter or width at slot 2442. Slot 2442 is not positioned in the center of bandage composition entry opening 2448 of inner nozzle cavity 2447. Instead, slot 2442 is off-center compared to bandage composition entry opening 2448. Slot 2442 is smaller in area than other slots shown herein and is generally circular or elliptical. Both outer nozzle cavity 2446 and an inner nozzle cavity 2447 are nonsymmetrical and are shaped differently than other dispensing nozzles shown herein. Some benefits of this off center shape could include the ability to apply the bandage to harder to reach rounded areas such as elbows/knees and ankles. Another potential benefit is that the tapper shape is bigger and more readily accessible.

Many changes may be made to specific dispensing nozzle 2400 shown in FIG. 24 while still falling within the scope of the present disclosure.

Figure 25:
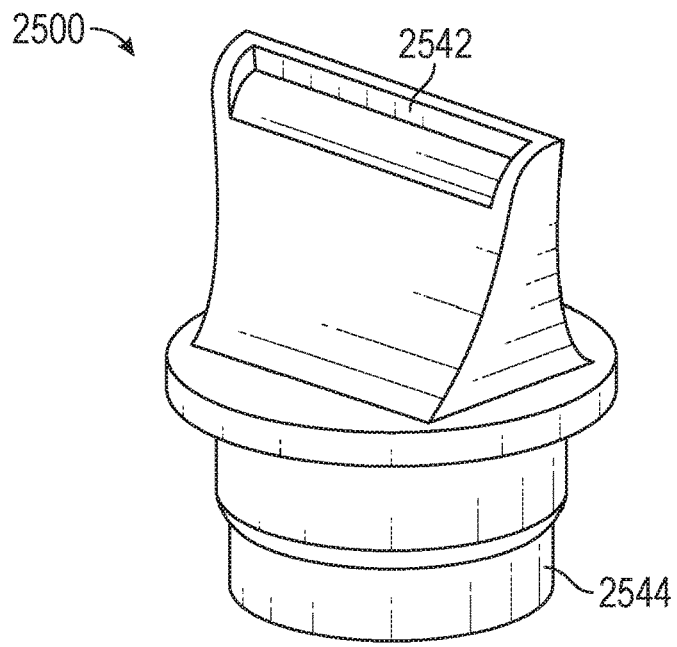
FIG. 25 is a perspective view of an alternative exemplary dispenser nozzle of a type generally described herein.
Figure 26A:
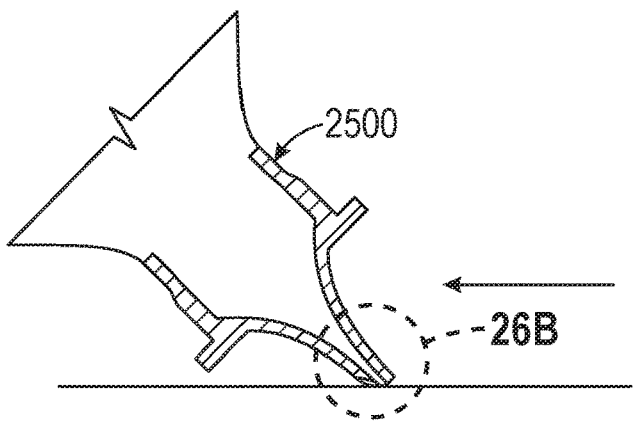
FIG. 26A is a schematic of the dispenser nozzle of FIG. 25 in use.
Figure 26B:
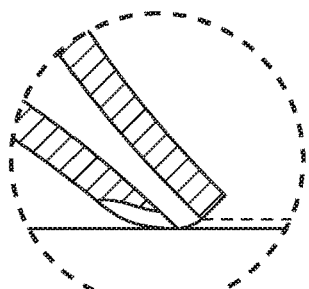
FIG. 26B is an exploded view of a portion of the dispenser nozzle of FIG. 26A in use.

FIG. 25 is a schematic view of an alternative embodiment of an exemplary dispensing nozzle of a type generally described herein. Dispensing nozzle 2500 includes, at one terminal end, a slot 2542 through which the bandage or dressing composition may be dispensed and, at the opposite terminal end, a nozzle head 2544 capable of attachment to a container. Dispensing nozzle 2500 is, in many ways, similar to other dispensing nozzles shown and/or described herein. Some differences of are as follows. Slot 2542 and/or the tip of dispensing nozzle 2542 is wider or has a larger diameter than nozzle head 2544. Slot 2542 is not planar, instead, it is angled or curved. Similarly, the tip of dispensing nozzle 2500 is not planar, instead, it is angled or curved. This non-planar, curved, angled, or offset feature of the tip or slot can provide advantages during application of the bandage or dressing composition. For example, this offset or angle can provide stability, assist the user in controlling the thickness of the bandage or dressing composition being applied, facilitate spreading of the bandage or dressing composition during application, and/or assist the user in achieving an even thickness and/or spread of the bandage or dressing composition across its applied length. FIGS. 26A and 26B are cross-sectional side views (and an enlarged cross-sectional side view in FIG. 26B) of the dispenser including the dispenser nozzle of FIG. 25 in use. From these figures, one can see how the angled, beveled, or offset slot 2542 or tip assists in providing at least some of these advantages.

Many changes may be made to specific dispensing nozzle 2500 shown in FIG. 25 while still falling within the scope of the present disclosure.

More information about each of the elements of the dispensers shown and described above is as follows.

Container

The container can be any shape, size, volume, or dimension capable of holding within it the desired bandage or dressing composition. Some exemplary containers are a single-piece construction. Some exemplary containers include multiple pieces.

Some exemplary container shapes include, for example, spheres, triangles, prisms, tubes, cylinders, squares, cubes, and similar shapes. Some exemplary containers include, for example, a tube, bottle, box, tottle (a combination of tube and bottle), pouch, syringe, and/or piston/platform displacement container (e.g., a stick deodorant dispenser in the United States). Some exemplary materials from which the container can be made include, for example, metal, laminate, plastic, glass, foil, multilayer film, cardboard, paper, polymer, and/or foil lined tetrapack.

Some exemplary container sizes include between about 2.5 inches to about 7 inches length and between about 0.5 inch to about 2 inches in width. Some exemplary containers have a length to width ratio of between about 5:1 and about 3.5:1. Some exemplary containers have a volume of between about 0.49 $in^3$ and about 22 $in^3$.

Some exemplary containers include the dispensing nozzle as part of the container. Some exemplary containers are of a one-piece construction including the dispensing nozzle. Some exemplary containers are capable of attachment to the dispensing nozzle. Some exemplary containers are capable of attachment to a cap. Some such embodiments include cap-container combinations that can be screw-fit together, snapped together, press-fit together, and other similar methods of attachment.

Dispensing Nozzle

The dispensing nozzle can be any shape, size, volume, or dimension capable of dispensing and/or holding the bandage or dressing composition. In many embodiments, the dispensing nozzle includes, at one terminal end, a slot, aperture, orifice, and/or opening through which the bandage or dressing composition may be dispensed and, at the opposite terminal end, a nozzle head capable of attachment to the container. In many embodiments, at least one nozzle cavity extends between the slot and nozzle head, and the nozzle cavity conveys and/or holds the bandage or dressing composition during its movement through the dispensing nozzle to the user's skin. Each of these elements are described in greater detail below.

Some exemplary dispensing nozzles have a volume of between about 0.00824 $in^3$ and about 0.038 $in^3$.

Some exemplary dispensing nozzles are capable of attachment to the container. Some such embodiments include dispensing nozzle-container combinations that can be screw-fit together, snapped together, press-fit together, and other similar attachment or connection methods. Some dispensing nozzles are part of the container. Some exemplary dispensing nozzles are of a one-piece construction with the container.

Some exemplary dispensing nozzles are capable of attachment to or mating with the cap. Some such embodiments include dispensing nozzle-cap combinations that can be screw-fit together, snapped together, press-fit together, and other similar connection or attachment methods. Alternatively or additionally, the dispensing nozzle and cap could be molded together as one piece with a living hinge or a tethered connection. In some embodiments, the dispensing nozzle-cap combination has one or more of an audible, tactile, and/or visual confirmation or signal that the dispensing nozzle and cap are securely and/or correctly combined, attached, or mated.

In some embodiments, it is desirable for the cap to be either "on" or "off" such that the cap will fall off when the container is flipped upside down if the cap is not correctly attached/engaged. In some embodiments, the cap can have features that make it "self-aligning" such that the user has clear confirmation with spinning, twisting, and/or push/pulling that the cap is correctly placed on the container to connect One exemplary embodiment is to align the bottom of the cap which allows the top of the cap to seat over the nozzle slot correctly. This method of aligning the cap would also make it easier to place a "wine stopper" or "tongue" piece in the top of the cap into the slot, if desired, without damaging the nozzle or making it too complicated for the user to align the two pieces.

Exemplary dispensing nozzles are made using injection or compression molding into a one-piece design. Alternative methods include casting. For a two-part construction, injection and/or compression molding can be used. The two parts could be connected with gluing or ultrasonic welding.

Nozzle Head

In some embodiments, the dispensing nozzle is part of the container, in which embodiments a nozzle head may be absent or may be present. Where present, the nozzle head can be part of the dispensing nozzle or part of the container.

Where present, the nozzle head may be capable of attachment to or mating with the container with which it will be used. Exemplary attachment mechanisms include screw fit, snap fit, press fit, and similar mechanisms. In some embodiments, the nozzle head can be permanently integrated into the container. In some embodiments, this can be accomplished by, for example, ultrasonic welding, gluing, and/or compressing molding. The nozzle head can have any desired shape, size, or dimension. Some exemplary nozzle head shapes include, for example, tubes, cylinders, spheres, triangles, prisms, squares, cubes, or other similar shapes.

In some embodiments, a portion of the nozzle head is matable with or attachable to the cap.

Nozzle head can have any desired aesthetic or decorative shape, dimension, or pattern including, for example, curves, notches, words, symbols, an embossed or raised pattern to impart/press a design onto the bandage composition, diamond, round, shoulders, cube(s), a paddle edge, a squeegee edge, and/or a design for spreading the composition once applied.

Nozzle Cavity

In many embodiments, one or more nozzle cavities extends between the slot and the nozzle head of the dispensing nozzle. The nozzle cavity can have any desired shape, size, and/or dimension, including having a varying cross-sections along its length or being tapered along its length. Some exemplary nozzle cavity shapes include, for example, cylindrical, tubular, rectangular, quadrilateral, elliptical, spherical, triangular, and similar shapes.

Many embodiments include a first or inner nozzle cavity that holds and/or conveys the bandage or dressing composition and a second or outer nozzle cavity that provides an aesthetically pleasing or decorative shape, size, or dimension to the dispensing nozzle. Additional nozzle cavities may be present.

Some exemplary inner nozzle cavity sizes include between about 0.5 inch to about 0.75 inch in length. Some exemplary inner nozzle cavity sizes include between about 0.25 inch and about 0.75 inch in thickness or depth. Some exemplary inner nozzle cavity sizes include between about 0.25 to about 0.75 inch in width. In some embodiments, the inner nozzle cavity has a volume of between about 0.00824 in$^3$ and about 0.038 in$^3$.

Some exemplary outer nozzle cavity sizes include between about 0.5 inch to about 1.5 inches in length. Some exemplary outer nozzle cavity sizes include between about 0.5 inch to about 1.5 inches in thickness or depth. Some exemplary outer nozzle cavity sizes include between about 0.5 inch to about 1.5 inches width. In some embodiments, the outer nozzle cavity has a volume of between about 0.033 in$^3$ and about 0.88 in$^3$, including the inner volume.

In some embodiments, the inner or outer nozzle cavity has a varying width or diameter along its length. In some embodiments, the inner nozzle cavity width or diameter at the nozzle head or container versus the inner nozzle cavity width at the slot has a ratio upper limit of around 1:1. Some exemplary inner or outer nozzle cavities are tapered from the slot to the nozzle head or container. Some exemplary nozzle cavities are tapered from the nozzle head or container to the slot. While any degree of draft may be used, some preferred embodiments draft the nozzle cavity at angle of between about 2 degrees and about 10 degrees. In some embodiments, such as, for example, that shown in FIG. 9A, the taper angle of the outer nozzle cavity is not a straight line but is instead a convex (not shown) or concave curve (as shown in FIG. 9A).

In some embodiments, the nozzle head includes a bandage or dressing composition entry opening through which bandage or dressing composition from the container flows into the inner nozzle cavity. In some embodiments, the bandage or dressing composition entry opening can have a diameter of between about 0.1 inch to about 1.0 inch. In some embodiments, the bandage or dressing composition entry opening can have a diameter of between about 0.25 inch to about 0.45 inch. In some embodiments, the ratio of the bandage or dressing composition entry opening width to the slot width is has an upper limit of about 1:1.

Slot:

The slot can have any desired shape, size, or dimensions. In some embodiments, the slot is preformed, meaning that its size is determined. In other words, it is not cut by the user at the time of use. In some embodiments, the slot forms the tip of the dispensing nozzle. In some embodiments, the slot has a length of between about 0.1 and about 1 inch and a width of between about 0.01 inch and about 0.1 inch. In some embodiments, the slot has a length of between about 0.2 and about 0.4 inch and a width of between about 0.01 inch and about 0.05 inch. In some embodiments, the slot can have an area of between about 0.001 in$^2$ to about 1 inch.

In some embodiments, the width of the bandage or dressing composition entry opening is the same as or larger than the width of the slot.

In some embodiments, the slot is not planar, instead, it is angled, curved, or beveled. This non-planar, curved, angled, or offset feature of the slot can provide advantages during application of the bandage or dressing composition, as is described herein with reference to FIGS. 25 and 26.

Cap:

The cap is capable of being placed on, attached to, and/or mated with the dispensing nozzle and/or container. The cap is also removable or can be removed from the dispensing nozzle and/or container. The cap is reusable such that it can be removed from and placed back onto the dispensing nozzle and/or container. The cap is thus configured to connect with either or both of the container and/or the dispensing nozzle of the dispenser of which the cap is a part. The cap includes an interior region and an outer surface or region.

The outer surface or region of the cap can match, approximate, and/or mimic the shape or size of the dispensing nozzle on which the cap is placed or can be different from the shape or size of the dispensing nozzle. The outer surface of cap can have any desired shape, size, dimension, pattern, or design. Some exemplary aesthetic or functional features of exemplary caps include curvilinear surfaces, one or more divots, concave or convex surfaces, tapering, symmetry, and/or asymmetry.

In some embodiments, the cap includes (1) a less or nonconformable portion or region including or made of a less or nonconformable material and (2) a conformable portion or region made of or including a more or conformable material. In some embodiments, the nonconformable portion or region includes the side walls or surface(s) of cap. In some embodiments, the conformable portion or region includes the top surface or region of the cap. In some embodiments, the top surface or region includes only or solely the conformable material. This is a significant difference over existing prior art where the cap was made of a less or nonconformable material that was subsequently at least partially filled with a conformable material. Instead, in at least some embodiments of the present disclosure, a portion (e.g., the top surface or region) of the cap is made solely of the conformable material. In some embodiments, this is an important feature because the conformability of this area of the cap assists in forming the air-tight seal with the slot that prevents the bandage or dressing composition from leaking from or drying out in the dispensing nozzle when the dispenser is not in use.

In some embodiments, the side walls or surface(s) of the cap include a nonconformable material (e.g., a harder, less resilient material) while the top or upper surface or region of the cap does not include the nonconformable material. In some embodiments, the side walls include both the conformable material and the less or nonconformable material. In some such implementations, the nonconformable material is used to provide the skeleton or walls of the cap and the conformable material is layered on top of the nonconformable material. The nonconformable material provides the structure and needed rigidity for the cap, and the conformable material provides a more friendly to the touch user experience as well as to provide good grip for the user when removing the cap.

In some embodiments, the conformable portion or region has a Shore A hardness of between about 20 and about 70 as measured by ASTM D2240-15 Standard Test Method for Rubber Property—Durometer Hardness. In some embodiments, the conformable portion or region has a hardness of between about 25 and about 35 A as measured by ASTM D2240-15 Standard Test Method for Rubber Property—Durometer Hardness. In some embodiments, the conformable portion or region includes at least one of thermoplastic polymer, a silicone, a thermoset elastomer, rubber, thermoplastic urethane, and similar materials. In some embodiments, the less or nonconformable portion or region has a shore A hardness of at least 1.2 times or 1.5 times or 1.7 times or 2.0 times, or 2.3 times, or 2.5 times, or 3 times the shore A hardness of the conformable portion as measured by ASTM D2240-15 Standard Test Method for Rubber Property—Durometer Hardness.

In some embodiments, the less or nonconformable portion or region has a Shore A hardness of at least about 24, at least about 26, at least about 28, at least about 30, at least about 32, at least about 35, at least about 38, and/or at least about 40 as measured by ASTM D2240-15 Standard Test Method for Rubber Property—Durometer Hardness. In some embodiments, less or nonconformable portion of region includes at least one of a thermoplastic (e.g., polypropylene), a resin, a thermoset plastic, urethane, acrylonitrile butadiene styrene, polytetrafluoroethylene, and/or a metal.

The cap also includes an inner or interior region having a size and shape that makes it amenable to being placed over a corresponding dispensing nozzle. In some embodiments, the cap is shaped and sized to fit over dispensing nozzle, so that the interior region of cap is sized slightly larger than the outer dimensions of the dispensing nozzle. In some embodiments, the inner region is configured to generally match, approximate, and/or mimic, the corresponding size and shape of the dispensing nozzle. In some embodiments, the inner region includes a preformed recess. In some embodiments, the preformed recess has an area of between about 0.0015 in$^3$ to about 2 in$^2$. In some embodiments, the preformed recess is made of the conformable material and thus forms an abutment surface that sealingly engages the preformed slot when the cap is attached to, mated with, or placed adjacent to the dispensing nozzle. The conformability of the conformable material assists in creating a seal between the abutment surface and the slot of the dispensing nozzle. This sealed engagement forms a tight seal. The presence of the recess is a significant difference over existing prior art that merely has a squishable material squeezed into a nonconformable container. In at least some embodiments of the present disclosure, the recess is preformed and designed to mate, pair, mirror, and/or match the preformed slot. This ensures that the seal is strong and tight through repeated uses.

In some embodiments, the dispensing nozzle and cap are connected. For example, the nozzle and cap could be connected by way of a hinge (e.g., a living hinge) or a tether.

Bandage or Dressing Composition:

Any of the bandage compositions of PCT Publication Nos. WO 2016/164315, WO 2016/164316, or U.S. Patent Application No. 62/407,922, all of which are incorporated herein in their entirety, can be used in conjunction with the dispensers described herein.

In some embodiments, the bandage or dressing compositions have a viscosity greater than 20.000 Centipoise (cps) when measured at 23° C. using a Brookfield LVT viscometer and the procedure described in either of PCT Publication Nos. WO 2016/164315 or WO 2016/164316. In some embodiments, the bandage or dressing compositions have a viscosity greater than 70,000 Centipoise (cps) when measured at 23° C. using a Brookfield LVT viscometer and the procedure described in either of PCT Publication Nos. WO 2016/164315 or WO 2016/164316. In some embodiments, the dispenser is suited for dispensing a gel composition having a viscosity of 200,000 to 800,000 cps (particularly 250,000 to 500,000 cps) and a wet coat weight of 50 to 120 mils at a generally uniform thickness. In some embodiments, the bandage or dressing composition is a gel.

In some embodiments, a film of dried bandage or dressing composition can have a thickness of at least 1, at least 1.5, 2, 4, or 8 mils and typically no greater than 25, 20, 15 mils, or 10 mils. As used herein, the term "mil" refers to 0.001 inch and 1 mil is equal to about 0.0025 centimeters or about 0.025 millimeters or about 25 micrometers. While the bandage or dressing compositions of the present disclosure can be coated in such a manner as to form a film having a uniform or substantially uniform thickness, variations in, for example, the pressure applied or the applicator used can result in variable thickness throughout the film layer. In presently preferred implementations, the thickness of the film over the target (e.g., wound or skin lesion) is at least 2 mils thick, while areas of the film surrounding the target (e.g., unblemished tissue) may exhibit a relatively thinner film thickness.

In some embodiments, the bandage or dressing composition can be conveniently stored at ambient conditions and can be provided in sterile form.

Preferred Methods of Use:

Any of the methods of use described PCT Publication Nos. WO 2016/164315, WO 2016/164316, or U.S. Patent Application No. 62/407,922, all of which are incorporated herein in their entirety, can be used in conjunction with the dispensers described herein.

In some embodiments, the area around the wound and/or the wound is cleaned and/or dried. A first quantity of bandage or dressing composition is dispensed from the dispenser onto an area proximate the target site and a substantially continuous layer of the bandage or dressing composition is created by drawing the applicator across the target site while dispensing the composition from the slot or tip of the dispensing nozzle. The dispenser can be held at an angle of between about 1 degree and about 180 degrees from the target site. Once the bandage or dressing composition reaches an area proximate the target site (e.g., one spaced from the wound) the dispenser is manipulated to sever the connection between the bandage or dressing composition and the applicator tip. The user may also sever the connection by hand or using another tool. Multiple layers may be used for larger wounds or smaller applicator tips. In one exemplary implementation, the continuous layer of bandage or gel composition has a substantially continuous thickness of about 100 mil as applied. In embodiments where the dispenser includes a tapping surface, the bandage or dressing composition can be smoothed and/or tapped down. In some instances, this may effect an enhanced seal around the target area. Once the desired amount of gel is dispensed at the desired thickness, the composition is allowed to dry to a film (typically 2-5 minutes).

The bandage or dressing composition need not be applied in direct contact with the entire target site. In certain implementations, the bandage or dressing composition may be applied over an antiseptic or antimicrobial composition, sutures, gauze, other topical compositions, and combinations thereof.

As referenced above, the applied bandage or dressing composition can be removed with relatively little force in a single continuous film without substantial desquamation of the underlying tissue. This desirable property can be enhanced by rolling the edges of the applied film toward the center of the target (or film itself) prior to removal. Rolling can, in certain circumstances, provide a graspable edge for a user or treating professional to engage and remove the film from the skin. For thinner films (e.g., less than 4 mils), it may be sufficient for the film to be removed in multiple pieces.

Another method involves dispensing the bandage or dressing composition into the top of the cap (in the concavity or divot) and then using the cap to create a bandage by flipping the cap over into the desired skin area to apply the bandage or dressing composition to the skin.

The recitation of all numerical ranges by endpoint is meant to include all numbers subsumed within the range (i.e., the range 1 to 10 includes, for example, 1, 1.5, 3.33, and 10).

The terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein."

Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention can be determined with reference to the appended claims, along with the full scope of equivalents to which such claims are entitled.

Various embodiments and implementations are described herein. These embodiments and implementations should not be construed as limiting the scope of the present application in any manner, and changes and modifications may be made without departing from the spirit and scope of present disclosure. Further, only some end uses have been discussed herein, but end uses not specifically described herein are included within the scope of the present application. As such, the scope of the present application should be determined by the claims.

What is claimed is:

1. A dispenser, comprising:
   a container containing a bandage or dressing composition;
   a dispensing nozzle having a shape and size and including a nozzle head that connects or mates with the container and a preformed slot for dispensing the bandage or dressing composition, wherein the dispensing nozzle is part of the container and/or capable of attachment to the container and further wherein the dispensing nozzle has an outer nozzle cavity extending between the nozzle head and the preformed slot, the outer nozzle cavity having two opposing straight sides and two opposing curvilinear sides; and
   a removable cap configured to connect with one of the container and/or the nozzle, wherein the removable cap includes an interior region having a size and shape configured to match the size and shape of the dispensing nozzle and connecting with the container and/or the dispensing nozzle by a screw fit mechanism, wherein the removable cap is self-aligning when the removable cap is twisted to a position where a top of the removable cap is properly seated over the preformed slot;
   wherein, when the cap is connected with the container or nozzle, the preformed slot of the dispensing nozzle mates with and/or nests within a preformed recess including a conformable material that forms an abutment surface that sealingly engages the preformed slot;
   wherein the cap further comprises:
   a nonconformable portion made of a less conformable material than the conformable material, and the less conformable material has a Shore A hardness of at least 1.2 times the Shore A hardness of the conformable material
   and wherein a top portion of the cap is substantially free of the less conformable material.

2. The dispenser of claim 1, wherein the bandage or dressing composition has a viscosity greater than 20,000 Centipoise (cps) when measured at 23° C. using a Brookfield LVT viscometer.

3. The dispenser of claim 1, wherein the slot has an area of between about 0.001 in$^2$ to about 1 in$^2$.

4. The dispenser of claim 1, wherein the dispensing nozzle has a ratio of a width of bandage or dressing composition entry cavity to slot width upper maximum of about 1:1.

5. The dispenser of claim 1, wherein the dispensing nozzle has a volume of between about 0.00824 in$^3$ and about 0.038 in$^3$.

6. The dispenser of claim 1, further including a tapping area.

7. The dispenser of claim 1, wherein the preformed recess has an area of between about 0.0015 in$^2$ to about 2 in$^2$.

8. The dispenser of claim 1, wherein the conformable material has a hardness of between about 30 shore A and about 70 shore A as measured by ASTM D2240-15 Standard Test Method for Rubber Property—Durometer Hardness.

9. The dispenser of claim 1, wherein the bandage composition when applied using the dispenser has a wet coat weight of 50 to 120 mils at a generally uniform thickness.

10. The dispenser of claim 1, wherein the bandage composition, when applied and dried, has a thickness of between about 1 mil and about 10 mils.

11. The dispenser of claim 1, wherein the dispensing nozzle is tapered from the slot to a nozzle head or container and the degree of draft is between about 2 degrees and about 10 degrees.

12. The dispenser of claim 1, wherein the two opposing curvilinear sides are convex.

13. The dispenser of claim 1, wherein the two opposing curvilinear sides are concave.

14. A dispenser, comprising:
a container containing a bandage or dressing composition;
a dispensing nozzle including a nozzle head that connects or mates with the container and a slot for dispensing the bandage or dressing composition, wherein the dispensing nozzle is part of the container and/or capable of attachment to the container and further wherein the dispensing nozzle has an outer nozzle cavity extending between the nozzle head and the preformed slot, the outer nozzle cavity having two opposing straight sides and two opposing curvilinear sides; and
a removable cap configured to connect with one of the container and/or the nozzle, wherein the removable cap includes an interior region having a size and shape configured to match the size and shape of the dispensing nozzle and connecting with the container and/or the dispensing nozzle by a screw fit mechanism, wherein the removable cap is self-aligning when the removable cap is twisted to a position where a top of the removable cap is properly seated over the preformed slot,
wherein, when the removable cap is connected with the container or nozzle, the slot of the dispensing nozzle sealingly engages a portion of the removable cap; and
wherein the removable cap includes a first material having a Shore A hardness of between about 30 and about 70 and a second material having a Shore A hardness of at least 1.2 times the Shore A hardness of the first material, and wherein a top portion of the cap is substantially free of the second material.

15. The dispenser of claim 14, wherein the slot sealingly engages a portion of the removable cap by mating with and/or nesting within a preformed recess in the removable cap that forms an abutment surface that forms the seal between the slot and the removable cap.

16. The dispenser of claim 14, wherein the bandage or dressing composition has a viscosity of greater than 20,000 Centipoise (cps) when measured at 23?C using a Brookfield LVT viscometer.

17. The dispenser of claim 14, wherein the slot has an area of between about 0.001 in$^2$ to about 1 in$^2$.

18. The dispenser of claim 14, wherein the dispensing nozzle has a ratio of a width of bandage or dressing composition entry cavity to slot width with an upper maximum of about 1:1.

19. The dispenser of claim 14, wherein the dispensing nozzle has a volume of between about 0.00824 in$^3$ and about 0.038 in$^3$.

20. The dispenser of claim 14, wherein the first material has a hardness of between about 20 Shore A and about 70 Shore A as measured by ASTM D2240-15 Standard Test Method for Rubber Property—Durometer Hardness.

21. The dispenser of claim 14, wherein the two opposing curvilinear sides are convex.

22. The dispenser of claim 14, wherein the two opposing curvilinear sides are concave.

* * * * *